(12) United States Patent
Singh et al.

(10) Patent No.: US 9,289,515 B2
(45) Date of Patent: Mar. 22, 2016

(54) MULTIVALENT FLUORESCENT PROBES

(71) Applicant: Caliper Life Sciences, Alameda, CA (US)

(72) Inventors: Rajendra Singh, San Jose, CA (US); Ning Zhang, Alameda, CA (US); Jae Beom Kim, Alameda, CA (US); Zhenjun Diwu, Alameda, CA (US)

(73) Assignee: Caliper Life Sciences, Alameda, CA (US)

( * ) Notice: Subject to any disclaimer, the term of this patent is extended or adjusted under 35 U.S.C. 154(b) by 0 days.

(21) Appl. No.: 14/679,513

(22) Filed: Apr. 6, 2015

(65) Prior Publication Data

US 2015/0209450 A1 Jul. 30, 2015

Related U.S. Application Data

(62) Division of application No. 13/236,211, filed on Sep. 19, 2011, now Pat. No. 9,012,242.

(60) Provisional application No. 61/403,688, filed on Sep. 20, 2010.

(51) Int. Cl.
  *G01N 33/58* (2006.01)
  *A61K 49/00* (2006.01)
  *G01N 33/533* (2006.01)

(52) U.S. Cl.
  CPC .......... *A61K 49/0021* (2013.01); *A61K 49/0032* (2013.01); *A61K 49/0052* (2013.01); *A61K 49/0056* (2013.01); *G01N 33/533* (2013.01); *G01N 33/582* (2013.01); *G01N 2333/9027* (2013.01); *G01N 2400/00* (2013.01)

(58) Field of Classification Search
  CPC ............... G01N 33/582; G01N 33/533; C09B 23/0066; C09B 23/0025; C09B 23/06; C09B 23/083
  See application file for complete search history.

(56) References Cited

U.S. PATENT DOCUMENTS

| | | | |
|---|---|---|---|
| 5,650,135 A | 7/1997 | Contag et al. | |
| 5,968,479 A | 10/1999 | Ito et al. | |
| 6,008,373 A | 12/1999 | Waggoner et al. | |
| 6,217,847 B1 | 4/2001 | Contag et al. | |
| 6,225,046 B1 | 5/2001 | Vesey et al. | |
| 6,303,757 B1 * | 10/2001 | Shigetou | G01N 33/532 436/800 |
| 6,307,029 B1 * | 10/2001 | Shigetou | G01N 33/531 436/800 |
| 6,649,143 B1 | 11/2003 | Contag et al. | |
| 6,890,515 B2 | 5/2005 | Contag et al. | |
| 6,908,605 B2 | 6/2005 | Contag et al. | |
| 6,916,462 B2 | 7/2005 | Contag et al. | |

(Continued)

FOREIGN PATENT DOCUMENTS

WO    WO 98/47538 A2    4/1998

OTHER PUBLICATIONS

Abe, et al., "Correlation of In Vitro Autofluorescence Endoscopy Images With Histopathologic Findings in Stomach Cancer," *Endoscopy* 32(4):281-286 (2000).

(Continued)

*Primary Examiner* — Shafiqul Haq
(74) *Attorney, Agent, or Firm* — Pasternak Patent Law; Dahna S. Pasternak

(57) ABSTRACT

Multivalent fluorescent probes and methods of using these multivalent fluorescent probes for in vitro and in vivo imaging are described.

12 Claims, 9 Drawing Sheets

(56) References Cited

U.S. PATENT DOCUMENTS

| | | | |
|---|---|---|---|
| 6,923,951 B2 | 8/2005 | Contag et al. | |
| 6,939,533 B2 | 9/2005 | Contag et al. | |
| 7,198,774 B2 | 4/2007 | Contag et al. | |
| 7,255,851 B2 | 8/2007 | Contag et al. | |
| 7,449,567 B2 | 11/2008 | Zhang et al. | |
| 7,449,615 B2 | 11/2008 | Contag et al. | |
| 8,669,374 B2 * | 3/2014 | Shen | C07D 401/14 435/6.1 |
| 9,012,643 B2 * | 4/2015 | Diwu | C09B 23/0025 435/7.21 |
| 2005/0171434 A1 | 8/2005 | Madden et al. | |
| 2005/0214221 A1 * | 9/2005 | Poss | A61K 49/0017 424/9.6 |
| 2008/0171351 A1 | 7/2008 | Smith | |
| 2008/0226562 A1 | 9/2008 | Groves et al. | |
| 2010/0331542 A1 | 12/2010 | Smith | |
| 2012/0077189 A1 * | 3/2012 | Shen | C07D 401/14 435/6.1 |

OTHER PUBLICATIONS

Alexander, et al., "Lasers Investigated as Diagnostic Tools for Breast Cancer," *J. Clin. Laser Med. Surg.* 9(6):416-418 (1991).

Boas, et al., "Scattering of Diffuse Photon Density Waves by Spherical Inhomogeneities Within Turbid Media: Analytic Solution and Applications," *Proc. Natl. Acad. Sci.* 91(11):4887-4891 (1994).

Gahlen, et al., "Spectrometry Supports Fluorescence Staging Laproscopy After Intraperitoneal Aminolaevulinic Acid Lavage for Gastrointestinal Tumours," *J. Photochem. Photobiol. B.* 52(1-3):131-135 (1999).

Hirsch, et al., "Early Detection of Lung Cancer: Clinical Perspectives of Recent Advances in Biology and Radiology," *Clin. Cancer Res.* 7:5-220 (2001).

Izuishi, et al., "Detection of Bile Duct Cancer by Autofluorescence Cholangioscopy: A Pilot Study," *Hepato-gastroenterol.* 46(26):804-807 (1999).

Jin, et al., "In Vivo Noninvasive Optical Imaging of Receptor-Mediated RGD Internalization Using Self-Quenched CY5-Labeled Raft-C(-RGDFK-)(4)," *Mol. Imaging* 6(1):43-55 (2007).

Kriegmair, et al., "5-Aminolevulinic Acid-Induced Fluorescence Endoscopy for the Detection of Lower Urinary Tract Tumors," *Urol. Int.* 63(1):37-31 (1999).

Leevy, et al., "Non-Invasive Optical Imaging of *Staphylococcus aureus* Bacterial Infections in Living Mice Using a Bis-Dipicolylamine-Zinc(II) Affinity Group Conjugated to a Near Infrared Fluorophore," *Bioconjugate Chem.* 19:686-692 (2008).

Licha, et al., "Synthesis and Characterization of Cyanine Dyes as Contrast Agents for Near-Infrared Imaging," *Proc. SPIE* 2927:192-198 (1996).

Lin, et al., "Novel Near-Infrared Cyanine Fluorochromes: Synthesis, Properties, and Bioconjugation," *Bioconj. Chem.* 13(3):605-610 (2002).

Major, et al., "In Vivo Fluorescence Detection of Ovarian Ovarian Cancer in the Nutu-19 Epithelial Ovarian Cancer Animal Model Using 5-Aminolevulinic Acid (ALA)," *Gynecol. Oncol.* 66(1):122-132 (1997).

Mycek, et al., "Colonic Polyp Differentiation Using Time-Resolved Autofluorescence Spectroscopy," *Gastrointest. Endosc.* 48(4):390-394 (1998).

Ntziachristos et al., "Concurrent MRI and Diffuse Optical Tomography of Breast Following Indocyanine Green Enhancement," *Proc. Natl. Sci.* 97(6):2767-2772 (2000).

Railton, et al., "Myocardial Scintigraphy with I-123 Heptadecanoic Acid as a Test for Coronary Heart Disease," *Euro. J. Nucl. Med.* 13(2):63-66 (1987).

Riedl, et al., "Fluorescence Detection of Bladder Tumors With 5-Aminolevulinic Acid," *J. Endourol.* 13(10):755-759 (1999).

Stepp, et al., "Fluorescence Endoscopy of Gastrointestinal Diseases: Basic Principles, Techniques, and Clinical Experience," *Endoscopy* 30(4):379-386 (1998).

Tearney, et al., "In Vivo Endoscopic Optical Biopsy With Optical Coherence Tomography," *Science* 276(5321):2037-2039 (1997).

Tearney, et al., "Catheter-Based Optical Imaging of a Human Coronary Artery," *Circulation* 94:3013 (1996).

Van Eenige, et al., "Clinical Value of Studies With Radioiodinated Heptadecanoic Acid in Patients With Coronary Artery Disease," *Eur. Heart J.* 11(3):258-268 (1990).

Ward, et al., "New Laser Techniques for Diagnosis and Treatment of Deep-Seated Brain Lesions," *J. Laser Appl.* 10:224-228 (1998).

White, et al., "Optical Imaging of Bacterial Infection in Living Mice Using Deep-Red Fluorescent Squaraine Rotaxane Probes," *Bioconjugate Chem.* 21(7):1297-1304 (2010).

Zaheer, et al., "In Vivo Near-Infrared Fluorescence Imaging of Osteoblastic Activity," *Nature Biotechnol.* 19:1148-1154 (2001).

* cited by examiner

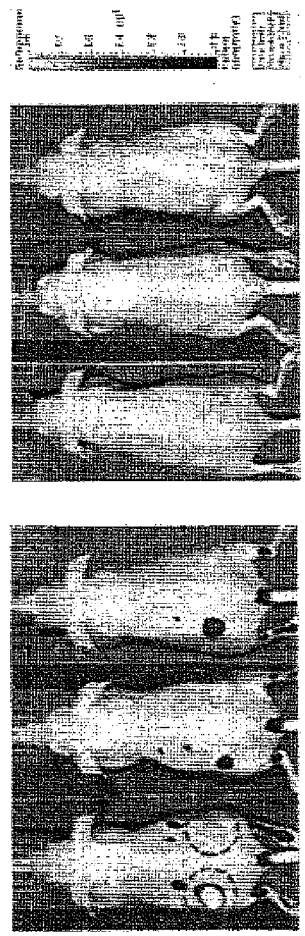
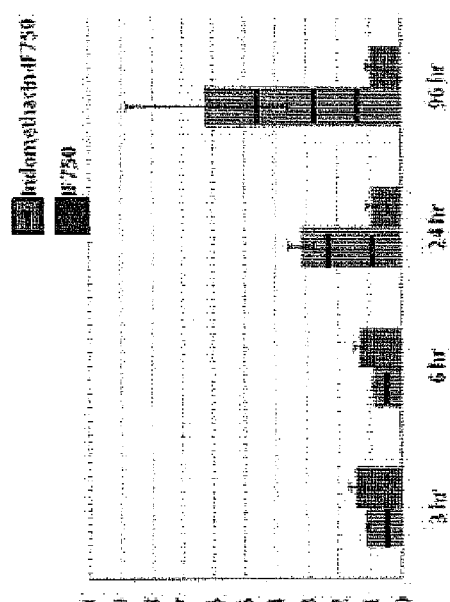
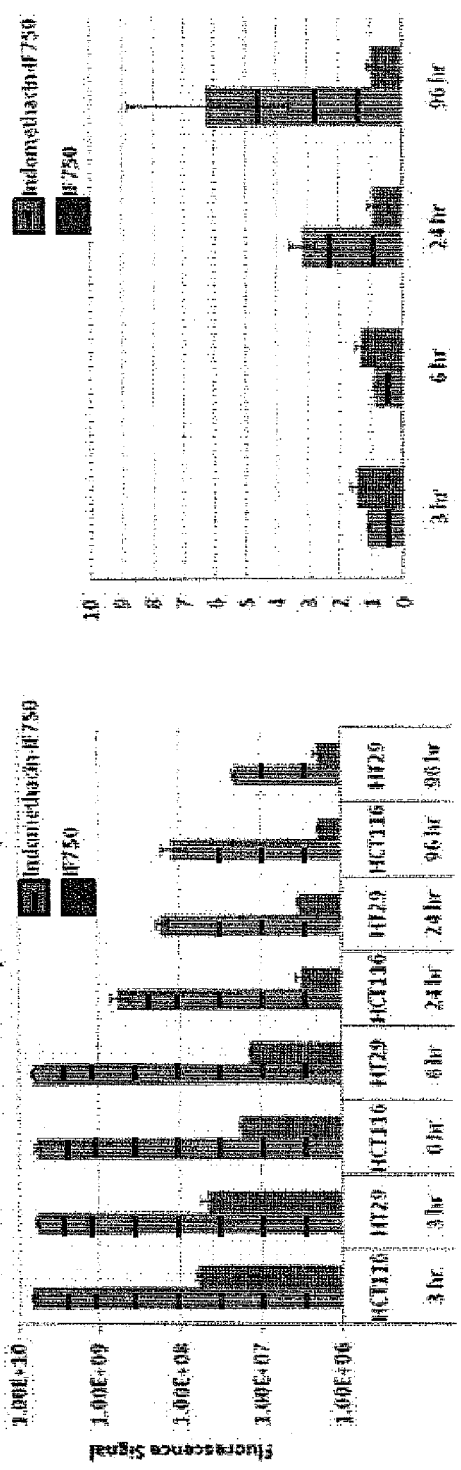
FIGURE 3

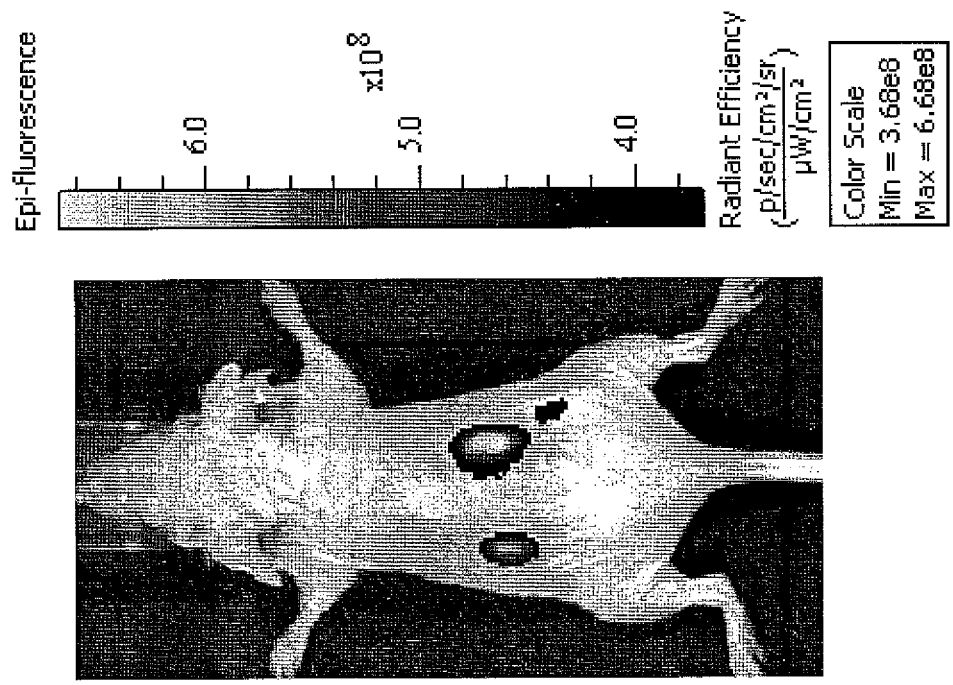
Figure 4B. RGD2900
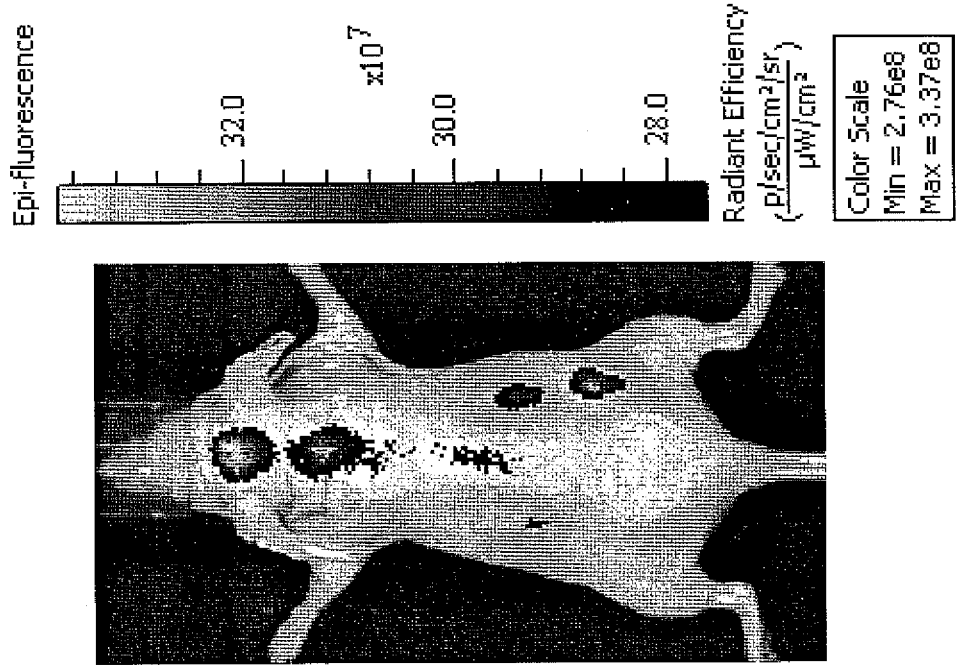
Figure 4A. RGD3500

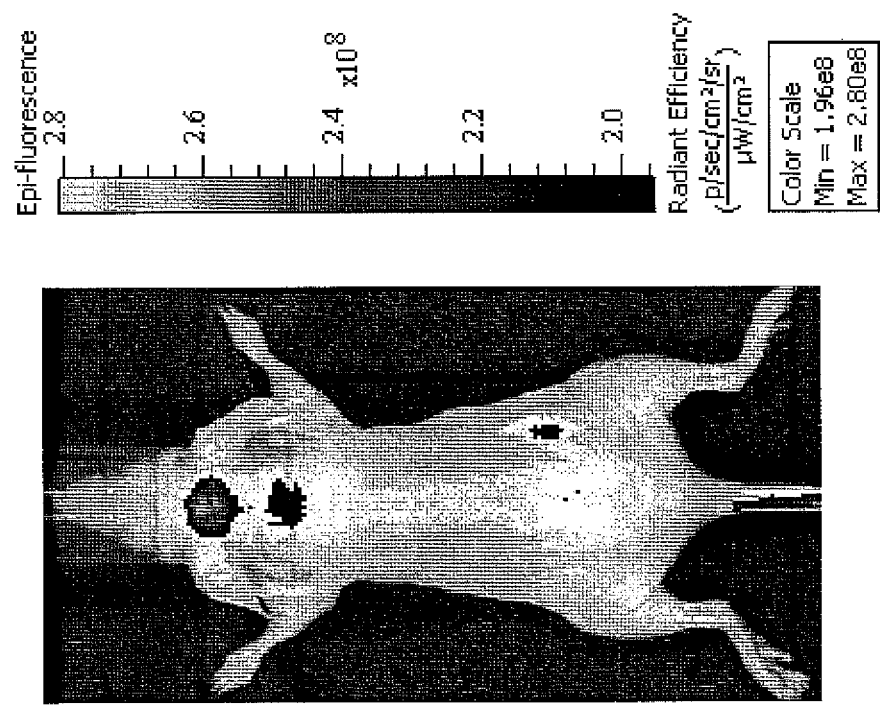
Figure 5B. RGD2-HPM2
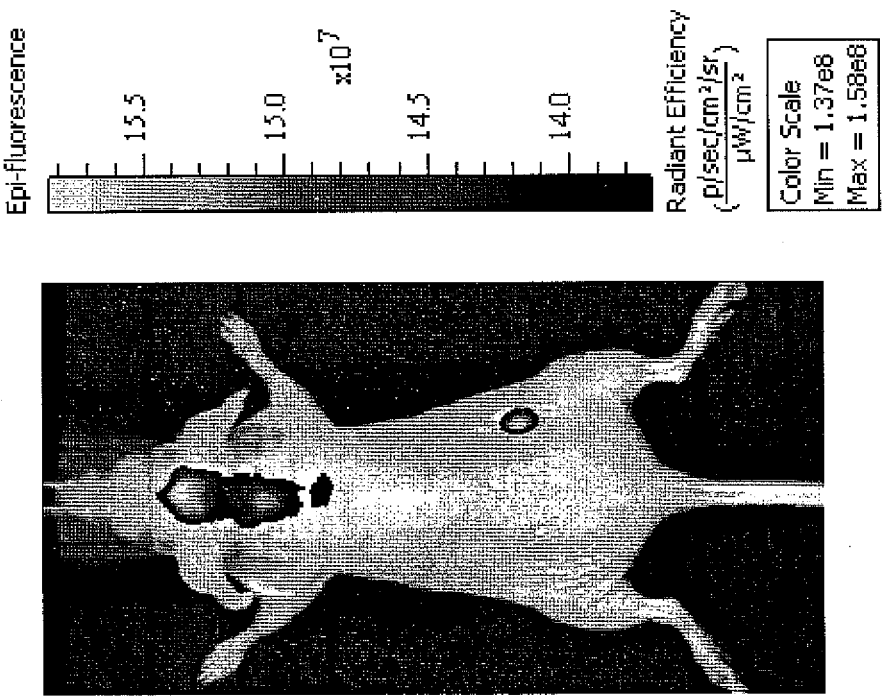
Figure 5A. RGD4

MULTIVALENT FLUORESCENT PROBES

CROSS-REFERENCE TO RELATED APPLICATIONS

The present application is a Divisional of U.S. patent application Ser. No. 13/236,211, filed Sep. 19, 2011 and claims the benefit of U.S. Provisional Application No. 61/403,688, filed Sep. 20, 2010, the disclosure of which is hereby incorporated by reference in its entirety.

TECHNICAL FIELD

The present disclosure is in the field of reagents for use in imaging. In particular, described herein are multivalent fluorescent probes that interact with cellular or extra-cellular target molecules using multiple targeting moieties.

BACKGROUND

Detection of light from cells, cell lysates and animals carrying a fluorescent probe is a powerful tool in diagnostics, drug discovery and medicine that allows for the identification of disease pathways, determination of mechanisms of action, evaluation of efficacy of drug compounds, and monitoring lead candidates' effects on disease progression (e.g., cancer, bacterial infection, etc.), trauma, cell death and the like in living animals. See, e.g., U.S. Pat. Nos. 7,449,615; 7,255,851; 7,198,774; 6,939,533; 6,923,951; 6,916,462; 6,908,605; 6,890,515; 6,649,143; 6,217,847; and 5,650,135.

Fluorescent probes are described in U.S. Patent Nos. 20050214221 and 20050171434. In addition, Jin et al. (2007) *Molecular Cancer* 6:43-55 describes in vivo imaging of RGD mediated internalization using the multivalent quenched RAFT-c(-RGDfK-) (4)-Cy5-SS-Q probe. U.S. Patent Publication No. 20080171351 describes optical imaging of bacterial infections using probes that target molecules (e.g., anionic phospholipids) present in the bacterial envelope. See, also, White et al. (2010) *Bioconjugate Chem.* 21:1297-1304 and Leevy et al. (2008) *Bioconjugate Chem.* 19:686-692.

However, despite the wide-spread use of imaging techniques, there remains a need a need for additional multivalent fluorescent probes.

SUMMARY

The present invention includes compositions comprising multivalent fluorescent probes and methods of using these fluorescent probes for imaging.

Thus, in one aspect, described herein is a multivalent fluorescent probe comprising one fluorochrome molecule chemically linked to a plurality (e.g., 2, 3, 4, 5, 6, 7, 8 or more) of targeting moieties. In certain embodiments, the fluorochrome is chemically linked to 3 or more (e.g., 3, 4, 5, 6, 7, 8 or even more) targeting moieties. In other embodiments, the fluorochrome is linked to 4 or more (e.g., 4, 5, 6, 7, 8 or even more) targeting moieties. The targeting moieties may all be the same molecules, some may be the same or they may all be different molecules.

In any of the fluorescent probes described herein, the targeting moieties can be small molecule, a sugar, a polypeptide, a cytokine, a neurotransmitter or the like (e.g., glucose, deoxyglucose, L-dopa, dopamine, thymidine, methionine, estradiol, acetate, raclopride, methyldiphosphonate, folate, a long-chain fatty acid, misonidazole, indomethacin and/or a therapeutic compound) or combinations thereof. The fluorochrome component of the fluorescent probes described herein can comprise any fluorescent material, for example a fluorescent dye (e.g., cyanine). In certain embodiments, the fluorochrome molecule has excitation and emission maximum between 550 nm and 1200 nm.

In another aspect, the disclosure provides methods of imaging using any of the fluorescent probes as described herein. In certain embodiments, the imaging methods are conducted in vitro, for example in cell culture systems, cell lysates, or isolated samples (e.g., tissue, blood, etc.). In other embodiments, the imaging methods are conducted in vivo (e.g., on an animal subject, such as a mouse, rat or human). In certain embodiments, the imaging methods comprise (a) administering to a subject one or more multivalent fluorescent probes as described herein; (b) exposing the subject to light of a wavelength of light that excites the fluorochrome of the fluorescent probe; and (c) detecting the optical signal (light) emitted by the fluorescent probe. The methods may further involve the step of, after administration, allowing the fluorescent probe time to localize in the target tissue prior to exposing the subject to a wavelength of light that excites the fluorochrome. In addition, in any of the methods described herein, the steps may be repeated at predetermined intervals thereby allowing for evaluation of emitted signal of the multivalent fluorescent probe in the subject over time and/or the light emitted by the fluorescent probe is used to construct an image (e.g., two or three dimensional image). In any of the methods described herein, steps (b) and (c) may be done using an endoscope, a camera (e.g., CCD camera), a catheter, tomographic systems, hand-held optical imaging systems, surgical goggles, or intraoperative microscope. Furthermore, any of the methods described herein may be performed sequentially or simultaneously with additional imaging methods (e.g., PET, MRI, CT, X-ray, etc.).

In another aspect, described herein are methods of evaluating a disorder or disease state (e.g., presence of the disease, absence of the disease or state of a disease) in a subject. The methods comprise imaging a multivalent fluorescent probe using any of the methods described herein, wherein the presence, absence, or level of light emitted by the fluorescent probe is used to evaluate the disorder or disease (e.g., disease state). In certain embodiments, the methods are used to evaluate the stage of the disorder or disease. In other embodiments, the methods are used to evaluate a therapeutic course of action for a treatment of the disorder or disease state. In certain embodiments, the presence of light is indicative of the state (and/or location) of disease. In other embodiments, the absence of light is indicative of the state (and/or location of disease. In yet other embodiments, the level of light is indicative of the state of disease (e.g., a different level of light than a control subject without the disease and/or a different level of light than previously detected from the subject). In any of the methods described herein, the disorder or disease is selected from the group consisting of a cancer, a cardiovascular disease, a neurodegenerative disease, an immunologic disease, an autoimmune disease, an inherited disease, an infectious disease (e.g., bacterial infection), a bone disease, trauma (e.g., injury), cell death and an environmental disease. Any cell type, tissue or organ can be monitored, including, for example, liver, kidney, pancreas, heart, blood, urine, plasma, eyes, CNS (brain), PNS, skin, solid tumors, etc.

In yet another aspect, provided herein are kits comprising any of the compositions as described herein for carrying out any of the methods described herein. In certain embodiments, the kits comprise, in separate or the same containers, a multivalent fluorescent probe (e.g., dye) as described herein. The kits may also comprise instructions regarding reconstitution of reagents, injection of reagents into live animals and/or imaging, normalization and validation protocols.

These and other embodiments will readily occur to those of skill in the art in view of the disclosure herein.

BRIEF DESCRIPTION OF THE FIGURES

FIG. 3 depicts imaging of mice having subcutaneous tumors injected with the indicated probes and imaged at the indicated time points. "Indomethacin-IF750" refers to the multivalent fluorescent probe (each probe including one molecule of the fluorescent dye IF750 linked to 4 molecules of indomethacin); and "control" refers to mice injected with the fluorescent dye IF750 alone. The graphs shows fluorescence signal (left graph) and fold difference (right graph) of animals imaged after injection of the multivalent Indomethacin-IF750 probe (left bars) as compared to the control animals (right bars).

FIGS. 4A and 4B, depict imaging of mice injected with PC3M-luc2 human prostate cancer cells and with the indicated probes and imaged 1 day after probe injection. "RGD4" (FIG. 4A) refers to a multivalent fluorescent probe in which each probe includes one molecule of the fluorescent dye IF750 linked to 4 molecules of RGD via 4 linkers and "RGD2-HPM2" (FIG. 4B) refers to a multivalent fluorescent probe in which each probe includes one molecule of fluorescent dye IF750 linked to 4 RGD molecules via 2 hydroxy propyl methyl linkers (2 RGD molecules per linker).

FIGS. 5A and 5B, depict imaging of mice injected with U87-MG-luc2 human prostate cancer cells and with the indicated probes and imaged 1 day after probe injection. "RGD4" (FIG. 5A) refers to a multivalent fluorescent probe in which each probe includes one molecule of the fluorescent dye IF750 linked to 4 molecules of RGD via 4 linkers and "RGD2-HPM2" (FIG. 5B) refers to a multivalent fluorescent probe in which each probe includes one molecule of fluorescent dye IF750 linked to 4 RGD molecules via 2 hydroxy propyl methyl linkers (2 RGD molecules per linker).

FIG. 6A depicts two exemplary probes in which one or more of the four "R" groups (targeting moieties) of Compound 6 (see Example 1) can be deoxyglucose (2-DG) and/or c(RGDyK). FIG. 6B shows another exemplary probe in which at least one "R" group (targeting moieties) can be bis(zinc(II)-dicolylamine) also referred to "DPA-Zn(2)" for targeting bacteria. It will be apparent that the same or different targeting moieties may be linked to a single fluorochrome, for example when the four R groups are DPA-Zn(2), the resulting probe is called "DPA Tetra," which includes four bis(zinc(II)-dicolylamine) molecules.

FIG. 7A shows imaging of a mouse using a DPA probe with a single bis(zinc(II)-dicolylamine) targeting moiety. FIG. 7B shows an image obtained from an animal injected with a multivalent (four (4) DPA-Zn bacterial targeting moieties) probe as described herein.

FIG. 8A depicts the ratio of bacterial signal to background PBS signal and shows that the multivalent ("DPA Tetra," right bar) probe exhibited greater specificity than the DPA probe ("DPA," left bar) for bacterial targeting. FIG. 8B shows the ratio of LPS to PBS in the different groups and demonstrates that the DPA probe ("DPA," left bar) detected fluorescence signals from LPS injected sites, indicating this probe may bind to infiltrating inflammatory cells as instigated by the LPS challenge. The lack of signal at the LPS sites in DPA-tetra injected mice ("DPA Tetra," right bar) as compared to the DPA probe indicate that the multivalent DPA-tetra probe provides for more specific detection of bacterial infection.

DETAILED DESCRIPTION

Figure 1:
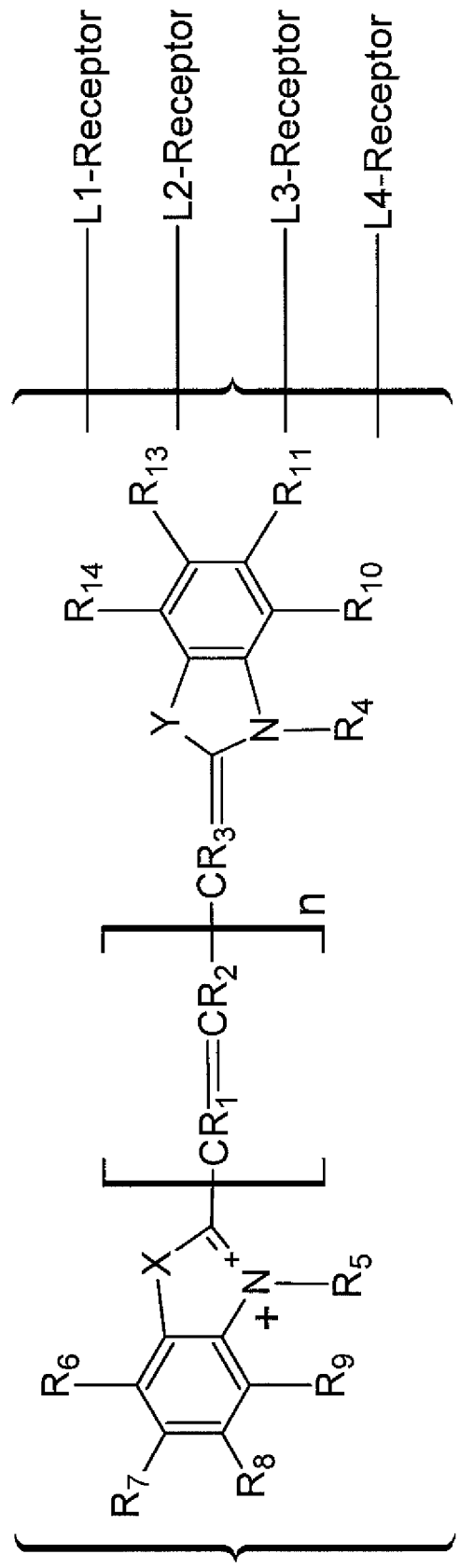
FIG. 1 depicts an exemplary multivalent fluorescent probe as described herein, in which X and Y are independently O, S, Se or $CR_{15}R_{16}$; n is 0 to 3. $R_1$ to $R_{17}$ are hydrogen, alkyl having from 1-20 carbons, alkoxy having from 1-20 carbons, trifluoromethyl, halogen, methylthio, sulfonyl, carbonyl, hydroxy, amino and thiol; L1, L2, L3 and L4 are independently a non-conjugated linker of 10-50 linear atoms selected from carbon, nitrogen, oxygen, phosphorus and sulfur that are further substituted by hydrogen, alkyl having from 1-20 carbons, alkoxy having from 1-20 carbons, trifluoromethyl, halogen, methylthio, sulfonyl, carbonyl, hydroxy, amino, thiol and/or any ligand that binds to a receptor (e.g., cell surface receptor).

The practice of the present invention will employ, unless otherwise indicated, conventional methods of chemistry, biochemistry, and recombinant DNA techniques, within the skill of the art. Such techniques are explained fully in the literature. See, e.g., A. L. Lehninger, *Biochemistry* (Worth Publishers, Inc., current addition); Sambrook, et al., *Molecular Cloning: A Laboratory Manual* (2nd Edition, 1989); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR (Introduction to Biotechniques Series)*, 2nd ed. (Newton & Graham eds., 1997, Springer Verlag); and *Methods In Enzymology* (S. Colowick and N. Kaplan eds., Academic Press, Inc.).

All publications, patents and patent applications cited herein, whether supra or infra, are hereby incorporated by reference in their entireties.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a nucleic acid" includes a mixture of two or more such nucleic acids, and the like.

"Light-generating" is defined as capable of generating light through a chemical reaction or through the absorption of radiation.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

A "fluorochrome" includes, but is not limited to, a fluorochrome, a fluorophore, a fluorochrome quencher molecule, or any organic or inorganic dye as well as nanoparticles such as quantum dots, polystyrene dyed particles, lanthanide chelates, radioactive isotopes (e.g., F18, C11, Y86, Ga68, Tc99, 1125 and In111), gadolinium chelates, manganese and iron oxide particles. Preferred fluorochromes include cyanine dyes and yellow, orange, red and near infrared fluorochromes (NIRFs) with preferred absorption (excitation) and emission maximum between 550 and 1200 nm. Typically, the multivalent probes described herein will also exhibit have (1) narrow excitation/emission spectrum, spectrally separated absorption and excitation spectra (i.e., excitation and emission maxima separated by at least 15 nm), (2) high chemical and photostability, (3) nontoxicity, (4) good biocompatibility, biodegradability and excretability, and (5) commercial viability and scalable production for large quantities (i.e., gram and kilogram quantities) required for in vivo and human use. Methods for measuring these parameters are known to one of skill in the art.

A "targeting moiety" or "ligand" is any molecule that can be used to target the fluorescent probes as described herein to a specific cell or other target. The ligand can include non-conjugated 10-50 linear atoms selected from carbon, nitrogen, oxygen, phosphorus and sulfur that are optionally further substituted by hydrogen, alkyl having from 1-20 carbons, alkoxy having from 1-20 carbons, trifluoromethyl, halogen, methylthio, sulfonyl, carbonyl, hydroxy, amino, thiol and/or one or more receptors molecules. Additional non-limiting examples of targeted moieties are described below.

By "linked" is meant connected by any attractive force between atoms strong enough to allow the combined aggregate to function as a unit. This includes, but is not limited to, chemical bonds such as covalent bonds (e.g., polar or non-polar), non-covalent bonds such as ionic bonds, metallic bonds, and bridge bonds, and hydrophobic interactions and van der Waals interactions.

2. General

Before describing the compositions and methods in detail, it is to be understood that the disclosure is not limited to particular formulations or process parameters as such may, of course, vary. It is also to be understood that the terminology used herein is for the purpose of describing particular embodiments only, and is not intended to be limiting.

Although a number of methods and materials similar or equivalent to those described herein can be used, exemplary preferred materials and methods are described herein.

Thus, the present disclosure relates to multivalent fluorescent probes (e.g., reagents) comprising a fluorochrome and 2 or more targeted moieties (e.g., 2, 3, 4, 5, 6, 7, 8, 9, 10 or more targeting moieties) attached to the single fluorescent molecule. This new class of multivalent fluorescent probe can be used for detection of molecular targets in a multitude of settings, such as in vitro, cell based, cell lysate based and in vivo assays. The multivalent (e.g., 4 or more targeting moieties per fluorochrome) described herein provide an unexpected advantage, for example in terms of specificity, over single or bivalent probes.

Typically, a single fluorochrome is coupled to multiple, spatially and chemically defined entities that are able to interact specifically with their putative targets. The multivalency is designed for optimal binding affinity via one or more linkers that minimize steric hindrance.

Any fluorochrome(s) can be used in the fluorescent probes described herein. The same or different fluorochromes may be used in the reagents described herein. Non-limiting examples of suitable fluorochromes include fluorescent dyes (e.g., cyanines, hemi-cyanines, azacarbocyanine, sulfo-benze-indocyanine, squarain, benzopyrylium-polymethine, and 2- or 4-chromenyliden based merocyanine dyes). Additional exemplary fluorochromes include the following: Cy5.5, Cy5, and Cy7 (Amersham Biosciences, Piscataway, N.J.); IRD38 and IRD78 (LI-COR, Lincoln, Nerb.); NIR-1 and IC5-OSu, (Dojindo, Kumamoto, Japan); AlexaFluor 660 and AlexaFluor 680, (Molecular Probes, Eugene, Oreg.); FAR-Blue, FAR-Green One, and FAR-Green Two (Innosense, Giacosa, Italy), ADS 790-NS and ADS 821-NS (American Dye Source, Montreal, Canada), Atto680 (Atto-Tec, Siegen, Germany), DY-680, DY-700, DY-730, DY-750, DY-782, (Dyomics, Jena, Germany), EVOBlue (Evotec, Hamburg, Germany) and indocyanine green (ICG) and its analogs and derivatives (Licha et al., 1996, SPIE 2927:192-198; U.S. Pat. No. 5,968,479), and indotricarbocyanine (ITC; WO 98/47538). Other examples of exemplary fluorochromes include Cy7.5 (Amersham Biosciences, Piscataway, N.J.), AlexaFluor 700 and AlexaFluor 750 (Molecular Probes, Eugene, Oreg.), FAR 5.5 (Innosense, Giacosa, Italy), fluorescent quantum dots (zinc sulfide-capped cadmium selenide nanocrystals) (QuantumDot Corporation, Hayward, Calif.), NIR2, NIR3, and NIR4 (Lin et al., 2002 Bioconj. Chem. 13:605-610) and chelated lanthanide compounds. Fluorescent lanthanide metals include europium and terbium. Fluorescence properties of lanthanides are described in Lackowicz, 1999, 15 Principles of Fluorescence Spectroscopy, 2nd Ed., Kluwar Academic, New York. See, also, U.S. Pat. Application No. 2002/0064794, PCT Publication No. WO 02/24815, U.S. Pat. No. 5,800,995, U.S. Pat. No. 6,027,709, PCT Publication No. WO 00/53678, PCT Publication No. WO 01/90253, EP 1273584, U.S. Patent Application No. 2002/0115862, EP 1065250, EP1211294, EP 1223197, PCT Publication No. WO 97/13810, U.S. Pat. No. 6,136,612, U.S. Pat. No. 5,268,486, U.S. Pat. No. 5,569,587, and Lin et al., 2002 Bioconj. Chem. 13:605-610, the entire teachings of which are incorporated herein by reference.

Fluorochromes may also include nanoparticles such as quantum dots, or polystyrene dyed particles, lanthanide chelates (for time resolved fluorescence) radioactive isotopes such as F18, C11, Y86, Ga68 for PET, Tc99, 1125 and In111 for SPECT, gadolinium chelates, manganese and iron oxide particles for MRI. See, also, U.S. Patent Publication No. 20080226562.

Any targeting moiety can also be used in the multivalent fluorescent probes as described herein. Any of the multivalent probes described herein may include one or more of the same or different targeting moieties. In certain embodiments, the targeting moiety comprises a ligand that binds to a cell surface receptor or molecule. Both cell surface receptors and molecules and ligands that bind specifically or non-specifically to receptors are known in the art. It will be apparent that the targeting moieties of the fluorescent probe may be bound on the surface of the cell (e.g., to an anionic phospholipid on a bacterial cell) or the probe may be internalized by the cell, for example upon binding of the targeting moieties to a cell surface receptor.

Thus, non-limiting examples of suitable targeting moieties include cytokines, hormones, growth factors, neurotransmitters, adhesion molecules and the like. Targeting moieties can also include any molecules produced, used, or recognized in carbohydrate metabolism, energy metabolism, fatty acid and lipid metabolism, nucleotide metabolism, amino acid metabolism, and co-factor and vitamin metabolism. (For current listing of metabolic pathways and metabolites see Boehringer Mannheim Biochemical Chart, available on the internet) (See also Salway (1999) Metabolism at Glance, Blackwell Science Inc; 2nd ed.). This includes, but is not limited to, molecules such as carbohydrates (e.g., glucose, galactose, mannose, glycosaminoglycans, etc.), organic acids (e.g., lactate, citrate, tartrate, acetate, etc.), amino acids (e.g., methionine, tyrosine, glutamate, taurine, ornithine, glutathione, etc.), halides (e.g., iodine, iodotyrosines chlorine, fluorine), steroids (e.g., estrogen, progesterone, testosterone, etc.), fatty acids (e.g., glycerol, palmitate, stearate, oleate, myrisates, etc.), lipids (e.g., cholesterol, phosphatidyl choline, ceramide, gangliosides, phospholipids such as anionic phospholipids, etc.), vitamins (e.g., thiamine, folate, biotin, riboflavin, niacin, etc.), nucleic acids and derivatives thereof (e.g., ATP, AMP, GTP, GMP, thiouracil, thymidine, urate, hypoxanthine, etc.), polypeptides and derivatives thereof, neurotransmitters (e.g., dopamine, serotonin, epinephrine, etc.), inorganic molecules (e.g., pyrophosphate, phosphate, phosphonates, sulfates, etc.), and drugs with proven action (e.g., therapeutic compounds).

In addition, synthetic derivatives of natural molecules may also be used, such as phosphonate derivatives in which the P—O—P bond is replaced by a non-hydrolyzable or metabolizable P—C—P bond could be used in probes of this invention. This includes but is not limited to bisphosphonates such as etidronate, clodronate, pamidronate, alendronate, tiludronate, risedronate, ibandronate, zoledronate, incadronate, olpadronate, neridronate, oxidronate, and methylene diphosphonate (MDP).

In certain embodiments, the targeting moiety comprises one or more small molecule drugs. For instance, many small molecule drugs are known in the art that are metabolically recognizable molecules, including drugs that are metabolically recognizable by any receptor or any enzyme (e.g., kinases such as serine, threonine, and tyrosine kinases). Non-limiting examples of enzymes that may be targeted include cytochrome P450, cyclooxygenase (COX) enzymes, and the like. Additional non-limiting examples of targeting moieties are deoxyglucose, thymidine, methionine, estradiol, danorubicin, acetate, dopamine, L-dopa, diprenorphine, methylspiperone, deprenyl, raclopride, phosphonates (e.g., methyldiphosphonates), tyrosine and methyltyrosines, glucoheptonate, folate, iodide, citrate, epinephrine, 1-aminocyclobutane-1-carboxylic acid, arachidonic acid, palmitic acid, glycosyl-phosphatidylinositol, myristic acid, farnesyl diphosphate, triglycerides, misonidazole, choline, vitamin B6 and its derivatives, and topotecan.

A single fluorochrome molecule can be linked to multiple targeting moieties (the same or different) using any suitable covalent or non-covalent linkages. In certain embodiments, the probes are made as described in Example 1 below.

It will be apparent that the any number of targeting moieties can in theory be linked to a single fluorochrome. In one embodiment, there are 3, 4, 5, 6, 7, 8 or 9 targeting moieties linked to single fluorochrome. In a preferred embodiment there are 4 targeting moieties linked to a single fluorochrome molecule. It will also be apparent that the same or different targeting moieties can be linked to the same fluorochrome. Furthermore, it will be apparent that one or more linkers can be used, for example one linker for each targeting moiety or multiple targeting moieties for one or more linkers.

Imaging

The fluorescent probes described herein can be used to imaging in vitro and in vivo using any suitable system according to the general principles of fluorescence, optical image acquisition, and image processing. For a review of optical imaging techniques, see, e.g., Alfano et al., 1997, Ann. NY Acad. Sci., 820:248-270.

An imaging system useful in the practice of this invention typically includes three basic components: (1) an appropriate light source for fluorochrome excitation, (2) a means for separating or distinguishing emissions from light used for fluorochrome excitation, and (3) a detection system. This system could be hand-held or incorporated into other useful imaging devices such as surgical goggles or intraoperative microscopes.

Preferably, the light source provides monochromatic (or substantially monochromatic) near infrared light. The light source can be a suitably filtered white light, i.e., bandpass light from a broadband source. For example, light from a 150-watt halogen lamp can be passed through a suitable bandpass filter commercially available from Omega Optical (Brattleboro, Vt.). In some embodiments, the light source is a laser. See, e.g., Boas et al., (1994) *Proc. Natl. Acad Sci. USA* 91:4887-4891; Ntziachristos et al. (2000) *Proc. Natl. Acad. Sci. USA* 97:2767-2772; and Alexander (1991) *J. Clin. Laser Med. Surg.* 9:416-418. Information on near infrared lasers for imaging can be found on the internet and various other well-known sources. A high pass or bandpass filter can be used to separate optical emissions from excitation light. A suitable high pass or bandpass filter is commercially available from Omega Optical.

In general, the light detection system can be viewed as including a light gathering/image forming component and a light detection/image recording component. Although the light detection system may be a single integrated device that incorporates both components, the light gathering/image forming component and light detection/image recording component will be discussed separately.

Thus, the multivalent fluorescent probes as described herein can imaged as described in U.S. Pat. Nos. 5,650,135 and 7,449,567 and as described in the materials provided by the manufacturer of the IVIS™ imaging systems, Caliper Life Sciences. In vivo imaging can be performed using the naked eye or any sort for camera (still or video). In certain embodiments, an intensified CCD camera sensitive enough to detect a bioluminescent signal and with wide enough dynamic range to also detect the fluorescent signal is used for imaging. Suitable cameras are known in the art and include, but are not limited to, an integrated imaging system (IVIS™ Imaging System, Caliper Life Sciences) controlled using LivingImage™ software (Caliper Life Sciences).

In other embodiments, the light gathering/image forming component is an endoscope. Endoscopic devices and techniques that have been used for in vivo optical imaging of numerous tissues and organs, including peritoneum (Gahlen et al. (1999) *J. Photochem. Photobiol.B* 52:131-135), ovarian cancer (Major et al. (1997) *Gynecol. Oncol.* 66:122-132), colon and rectum (Mycek et al. (1998) *Gastrointest. Endosc.* 48:390-394; Stepp et al., (1998) *Endoscopy* 30:379-386), bile ducts (Izuishi et al. (1999) *Hepatogastroenterology* 46:804-807), stomach (Abe et al. (2000) *Endoscopy* 32:281-286), bladder (Kriegmair et al. (1999) *Urol. Int.* 63:27-31; Riedl et al., (1999) *J. Endourol.* 13:755-759), lung (Hirsch et al. (2001) *Clin. Cancer Res.* 7:5-220), and brain (Ward (1998) *J. Laser Appl.* 10:224-228) can be employed in the practice of the present invention.

Other types of light gathering components useful in the invention are catheter-based devices, including fiber optics devices. Such devices are particularly suitable for intravascular imaging. See, e.g., Teamey et al. (1997) *Science* 276:2037-2039; and Teamey et al. (1996) *Circulation* 94:3013.

Still other imaging technologies, including phased array technology (Boas et al. (1994) *Proc. Natl. Acad. Sci. USA* 91:4887-4891; Chance (1998) *Ann. NY Acad. Sci.* 838:29-45), optical tomography (Cheng et al. (1998) *Optics Express* 3:118-123; Siegel et al. (1999) *Optics Express* 4:287-298), intravital microscopy (Dellian et al. (2000) *Br. J. Cancer* 82:1513-1518; Monsky et al. (1999) *Cancer Res.* 59:4129-4135; Fukumura et al. (1998) *Cell* 94:715-725), confocal imaging (Korlach et al. (1999) *Proc. Natl. Acad. Sci. USA* 96:8461-8466; Rajadhyaksha et al. (1995) *J Invest. Dermatol.* 104:946-952; Gonzalez et al. (1999) *J Med.* 30:337-356), and fluorescence mediated tomography (Nziachristos et al. (2002) *Nature Medicine* 8:757-760) can be employed in the practice of the present invention.

Any suitable light detection/image recording component, e.g., charge coupled device (CCD) systems or photographic film, can be used in the invention. The choice of light detection/image recording will depend on factors including type of light gathering/image forming component being used. Selecting suitable components, assembling them into a near infrared imaging system, and operating the system is within ordinary skill in the art.

The compositions and methods of the present invention may be used in combination with other imaging compositions and methods. For example, the methods of the present invention may be used in combination with other traditional imaging modalities such as X-ray, CT, PET, SPECT, and MRI. For instance, the compositions and methods of the present invention may be used in combination with CT and MRI to obtain both anatomical and metabolic information simultaneously. It will be apparent that when in combination with X-ray, CT, PET, SPECT, and MR contrast agents, the multivalent fluorescent probes of the present inventions may also contain components, such as iodine, gadolidium atoms, and radioactive isotopes, which can be detected using CT, PET, SPECT, and MR imaging modalities in combination with optical imaging as described herein.

The fluorescent probes of the present invention may be also be constructed using molecules with various magnetic properties, such as iron oxide nanoparticles. These dual optical/MR imaging probes can be used for imaging not only the metabolic activity of a variety of different disease states by measuring the optical signal, but also their precise localization from their effects on T2 weighted MR images (Josephson et al. (2002) *Bioconj. Chem.* 13:554-560).

The reagent containing the multivalent fluorescent probe can be administered to a live animal using any suitable delivery route, for example intraperitoneal, subcutaneous, intravenous, mucosal or other delivery route.

In certain embodiment, the method includes the steps of: (a) administering to a subject an multivalent fluorescent probe as described herein; (b) allowing time for the multivalent fluorescent probe to reach the target tissue and, preferably, but not necessarily, for molecules in the target tissue to metabolize the probe; (c) illuminating the target tissue with light of a wavelength absorbable by the multivalent fluorescent probe; and (d) detecting the signal emitted by the multivalent fluorescent probe.

These steps can also be repeated at predetermined intervals thereby allowing for the evaluation of emitted signal of the multivalent fluorescent probe in a subject or sample over time. The emitted signal may take the form of an image. The subject may be a mammal, including a human. The subject may also be non-mammalian, (i.e., *C. elegans, drosophila*, etc.). The sample can include, without limitation, cells, cell culture, tissue sections, cytospin samples, or the like. As noted above, similar methods can be carried out to perform in vitro imaging, for example on cell or tissue samples.

In certain embodiments, two or more multivalent fluorescent probes are imaged simultaneously. The method includes administering to a subject two or more multivalent fluorescent probes, either at the same time or sequentially, whose optical properties are distinguishable from that of the others. The method therefore allows the recording of multiple events or targets. Similar methods can be carried out to perform in vitro imaging, for example on cell or tissue samples.

In other embodiments, the method comprise imaging one or more multivalent fluorescent probe(s) as described herein, simultaneously with one or more additional imaging probes, for example, magnetic resonance, CT, X-ray, ultrasound, or nuclear medicine imaging modalities or agents. The method includes administering to a subject one or more imaging probes, either at the same time or sequentially, including at least one multivalent fluorescent probe as described herein, whose properties are distinguishable from that of the others. The method therefore, allows the recording of multiple events or targets using more than one imaging modality or agent. Similar methods can be carried out to perform in vitro imaging, for example-on cell or tissue samples.

The methods as described herein can be used to determine a number of indicia, including tracking the localization of the multivalent fluorescent probes in the subject over time or assessing changes or alterations in the metabolism of the multivalent fluorescent probe in the subject over time. The methods can also be used to follow therapy for such diseases by imaging molecular events modulated by such therapy, including but not limited to determining efficacy, optimal timing, optimal dosing levels (including for individual patients or test subjects), and synergistic effects of combinations of therapy.

The invention can be used to help a physician or surgeon to identify and characterize areas of disease, such as colon polyps or vulnerable plaque, to distinguish diseased and normal tissue, such as detecting tumor margins that are difficult to detect using an ordinary operating microscope, e.g., in brain surgery, and help dictate a therapeutic or surgical intervention, e.g., by determining whether a lesion is cancerous and should be removed or non-cancerous and left alone. Detection of inflammation, apoptosis and bacterial infection can also be accomplished using the compositions and methods described herein.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring drug therapy. Examples of such disease or disease conditions include any type of inflammation (e.g., inflammation caused by arthritis, for example, rheumatoid arthritis), bacterial infection, all types of cancer (e.g., detection, assessing treatment efficacy, prognosis, characterization), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections), immunologic disease (e.g., Acquired Immunodeficiency Syndrome, lymphoma, multiple sclerosis, rheumatoid arthritis, diabetes mellitus), central nervous system disease or trauma (e.g., Parkinson's disease, Alzheimer's disease, brain trauma), and bone-related disease (e.g., osteoporosis, primary and metastatic bone tumors, osteoarthritis). Other diseases that can be assessed include neurodegenerative diseases, autoimmune diseases, inherited diseases, and environmental diseases. The methods of the invention can therefore be used, for example, to determine the presence of tumor cells and localization of tumor cells, the presence and localization of inflammation, the presence and localization of vascular disease including areas at risk for acute occlusion (vulnerable plaques) in coronary and peripheral arteries, regions of expanding aneurysms, unstable plaque in carotid arteries, and ischemic areas. The methods of the invention can also be used in identification of apoptosis (cell death), necrosis, and hypoxia.

It is well known that malignant tissue may be easily distinguished from benign or normal tissue by its increased rate of glucose metabolism. Specifically, rapidly dividing cells have been shown to exhibit enhanced glucose metabolism, a requirement necessary to sustain their increased need for ATP generation and substrate storage. In addition to normal physiologically-related growth processes, cancer cell growth is heavily dependent upon increased glucose metabolism. Furthermore, the correlation between increased glucose metabolism and tumor growth has been well documented and exploited in the development of drugs aimed at blocking glucose metabolism for therapeutic purposes. Glucose transport across cell membranes requires the presence of specific integral membrane transport proteins, which includes the facilitative glucose carriers.

Thus, in certain embodiments, the multivalent probes described herein include 3, 4 or more targeting moieties that are taken up by a glucose transport system and are therefore indicative of cancer. See, Examples. Therefore, a preferred embodiment of the present invention for imaging glucose metabolism is comprised of 1-30 (e.g., 4) glucose or deoxyglucose molecules chemically linked to a suitable fluorochrome for use in diagnosing and staging tumors, myocardial infarctions and neurological disease.

In other embodiments, the multivalent probes described herein are used to image diseased tissue is in the central nervous system. For example, the density of dopamine transporters and level of dopamine metabolism in the central nervous system is known to be elevated or decreased in a number of different disease states including Parkinson's disease, Tourette's Syndrome, Lesch-Nyhan Syndrome, Rhett's Syndrome, and in substance abusers. Proper dopamine metabolism also is required to maintain a state of psychological well-being. Thus, for imaging of increased or decreased levels of dopamine transporters and level of dopamine metabolism, some or all of the targeting moieties may bind to the dopamine transporter (DAT). Such dopamine transporter-binding molecules include, but are not limited to, L-dopa and tropanes.

In another embodiment, the multivalent probes described herein are used to image diseased tissue is in the cardiovascular system, for example using targeting moieties comprising long chain fatty-acids, as the synthesis and breakdown of long-chain fatty acids are indicative of various cardiac diseases including coronary artery disease, myocardial infarction, cardiomyopathies, and ischemia (Railton et al. (1987) *Euro. J NucL. Med.* 13:63-67; and Van Eenige et al. (1990) *Eur. Heart J.* 11:258-268).

In yet another embodiment, the multivalent probes described herein are used to image imbalances in osteoblast activity, which can be indicative of several disease states including osteoporosis, osteoblastic cancer metastases, early calcification in atherosclerosis and cancer lesions, arthritis and otoslcerosis. Phosphonates and analogs thereof localize in areas where osteoblast activity is high, including areas of active bone remodeling (Zaheer et al. (2001) *Nature Biotech* 19:1148-1154). Thus, for imaging bone diseases, atherosclerosis and otoslcerosis a multivalent probe comprising methylene diphosphonate, pyrophosphate, and/or alendronate molecules can be used.

The multivalent probes described herein can also be used for imaging of tissues for hypoxia, for example tumors and infarcted regions that are known to be hypoxic when compared to normal or unaffected tissue. Targeting moieties such as nitroimidizoles (e.g., misonidazole) are known in the art to preferentially accumulate and be retained in hypoxic areas. In cells with reduced oxygen content, these compounds are metabolized by cellular reductases, such as xanthine oxidase, and subsequently become trapped inside the cell. Therefore, for imaging hypoxia, multivalent probes as described herein can comprise 3, 4 or more misonidazole molecules chemically linked to a fluorochrome.

The multivalent probes as described herein can also be used for imaging of bacterial infection, for example using probes comprising targeting moieties that recognize molecules specific for bacteria. Targeting moieties known to target bacterial cells are known in the art. See, e.g., U.S. Patent Publication Nos. 20080171351 and 20100331542; White et al. (2010) *Bioconjugate Chem.* 21:1297-1304 and Leevy et al. (2008) *Bioconjugate Chem.* 19:686-692 for molecules directed to bacterial phospholipids. Therefore, for imaging of bacterial infection as well as inflammation and apoptosis, multivalent probes (e.g., 4 or more targeting moieties per fluorochrome) as described herein provide enhanced imaging of bacterial infection without the need to genetically engineer the bacteria.

Kits

The present invention also provides kits comprising the reagents described herein and for carrying out the methods described herein. In particular, these kits typically include one or more pre-made multivalent fluorescent probe or individual elements of the fluorochrome and targeting moieties. The kit optionally includes buffers and containers as well as written instructions for carrying out the methods described herein. In the case of prepackaged reagents, the kits optionally include pre-measured or pre-dosed reagents that are ready to incorporate into the methods without measurement, e.g., pre-measured fluid aliquots, or pre-weighed or pre-measured solid reagents that may be easily reconstituted by the end-user of the kit.

3. Experimental

Below are examples of specific embodiments for carrying out the present disclosure. The examples are offered for illustrative purposes only, and are not intended to limit the scope of the present disclosure in any way.

Example 1

Chemical Synthesis

A. Preparation of Compound 1

To prepare compound 1, shown below, to the solution of sodium ethoxide (40 g sodium in 500 mL dry ethanol) was added ethyl 2-methylacetoacetate (250 g), followed by ethyl 6-bromohexanonate (445 g). The mixture was heated to reflux for 2 days. After cooling to room temperature, the mixture was filtered and the filtrate was concentrated. The residue was treated with 1M HCl to pH 1 and the aqueous solution was extracted with chloroform twice. The organic layer was washed with brine and dried over $Na_2SO_4$. After removal of solvent, the residue was purified on silica gel to give ethyl 2-(5-ethoxycarbonyl)pentyl-2-methylacetoacetate.

The above acetoacetate (136 g) in methanol (1000 mL) was mixed with a solution of NaOH (66 g) in water (60 mL). The mixture was stirred at 50° C. for 3 hours. After removal of methanol, the residue was acidified with 1M HCl to pH 2. The aqueous solution was extracted with EtOAc(3×500 mL). The organic layer was washed with brine and dried over $Na_2SO_4$. The crude product was purified with silica gel chromatography to yield Compound 1.

Compound 1

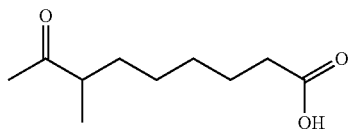

B. Preparation of Compound 2

To prepare Compound 2 (shown below), Compound 1 (42 g) and 4-hydrazinobenzenesulfonic acid (43 g) in acetic acid (30 mL) was heated to reflux for 8 hours. After removal of the solvent, the residue was purified on silica gel to give Compound 2.

Compound 2

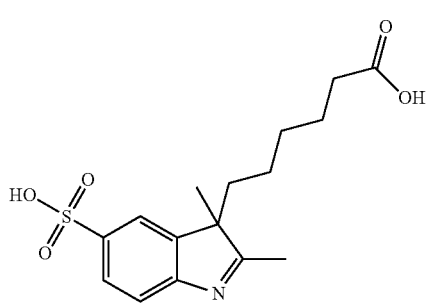

C. Preparation of Compound 3

To prepare Compound 3, a solution of Compound 2 (30 g) was heated with 6-bromohexanoic acid (50 g) in 1,2-dichlorobenzene (10 mL) at 110° C. overnight. The mixture was cooled to room temperature and 1,2-dichlorobenzene was decanted. The solid was triturated with ethyl ether and the free powder was filtered and washed with ether and dried under vacuum to yield Compound 3.

Compound 3

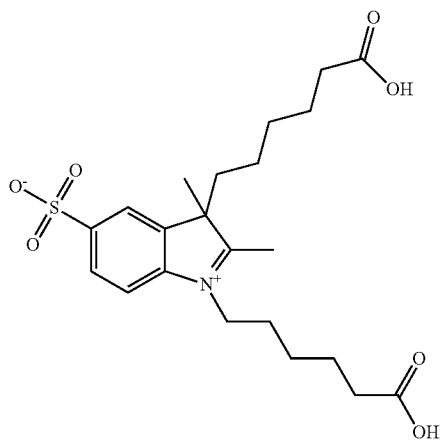

D. Preparation of Compound 4

To a solution of Compound 2 (2.3 g) in DMF (30 mL) was added O—(N-succinimidyl)-N,N,N',N'-tetramethyluronium tetrafluoroborate (3.6 g), followed by triethylamine (5 mL). The mixture was stirred at room temperature for 2 h. The solution was poured into EtOAc (500 mL). The solid was centrifuged and washed with EtOAc (3×500 mL), ether (3×500 mL) and dried under vacuum to give Compound 4.

Compound 4

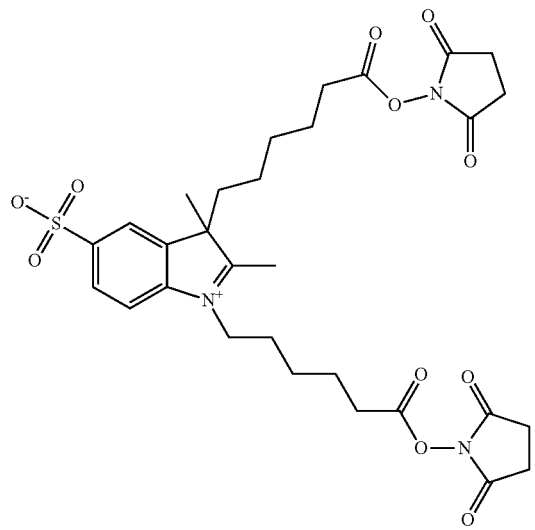

E. Preparation of Compound 5

The above di-succinimidyl ester of Compound 4 (130 mg) was dissolved in DMF (10 mL) and a solution of glucosamine (200 mg) in water (2 mL) (neutralized with $Na_2CO_3$ (pH 8.5) was added slowly during the period of 30 minutes. The mixture was stirred at room temperature overnight. After removal of solvent, the residue was purified by preparative HPLC to give Compound 5.

Compound 5

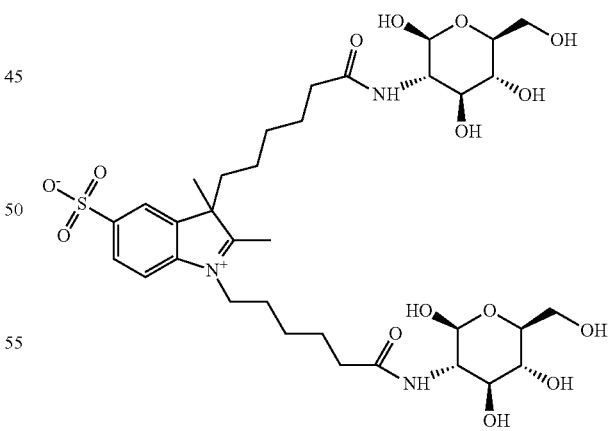

F. Preparation of Compound 6

Figure 6A:
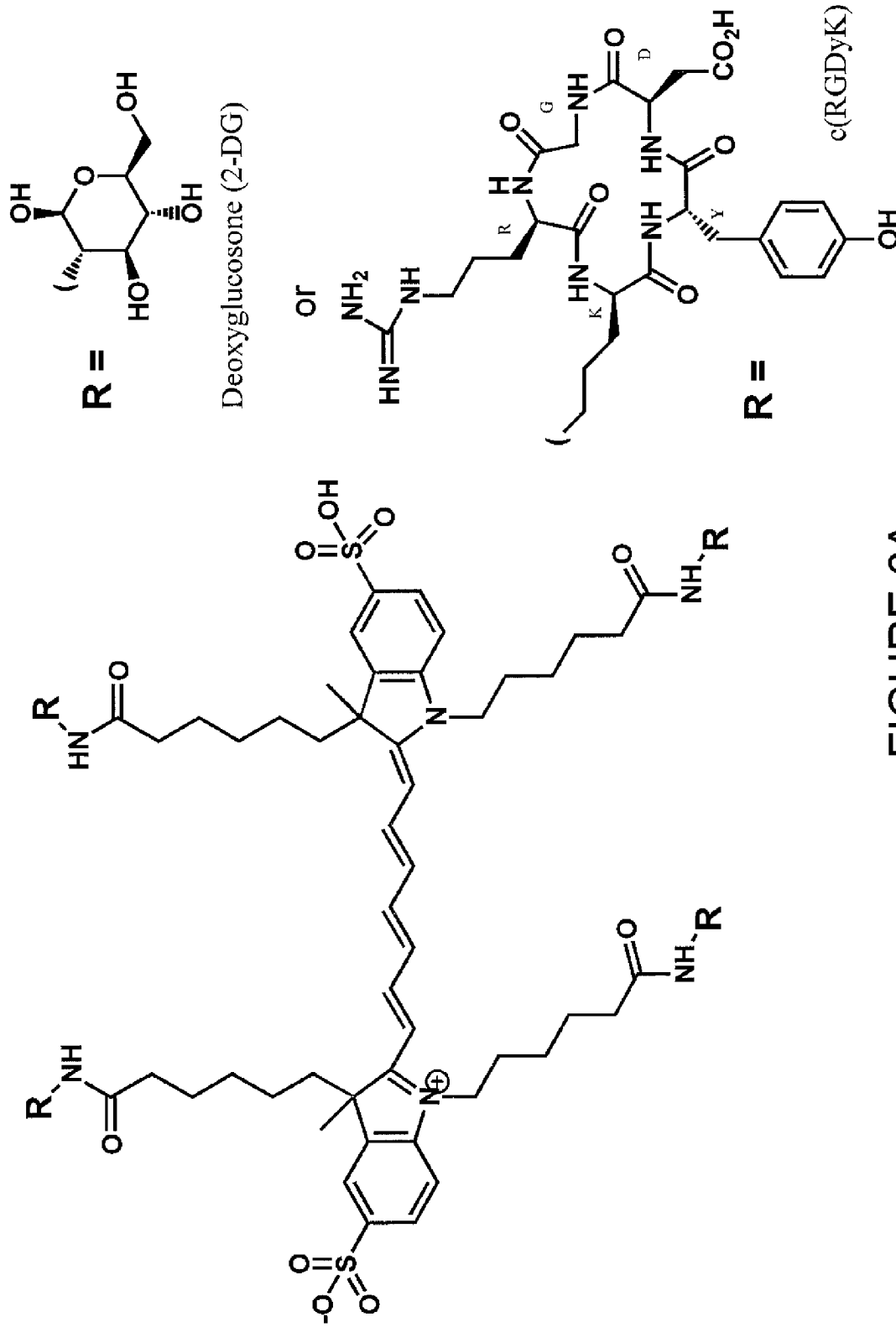
FIGS. 6A and 6B, depict exemplary targeting moieties as described herein.
Figure 6B:
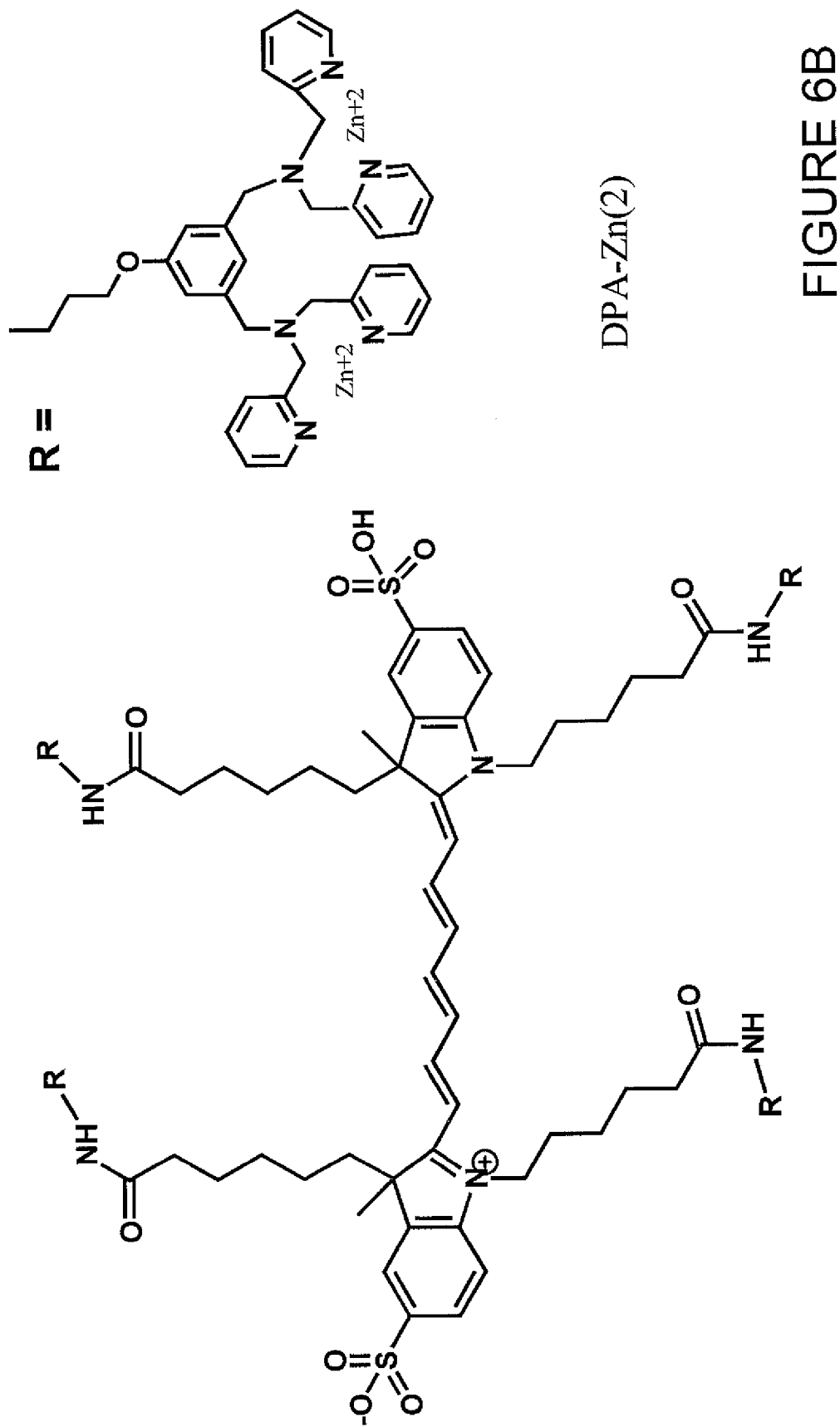

A solution of Compound 5 (50 mg) and glutaconaldehyde dianil hydrochloride (10 mg) in pyridine (1 mL) and acetic anhydride (0.5 mL) was heated at 120° C. for 1-2 hours. The completion of the reaction was monitored by absorption spectra in methanol. The reaction mixture was cooled and poured into ethyl acetate (50 mL). The crude product was collected by centrifugation and washed with ethyl acetate twice. Preparative HPLC purification gives Compound 6. See, also, FIG. 6.

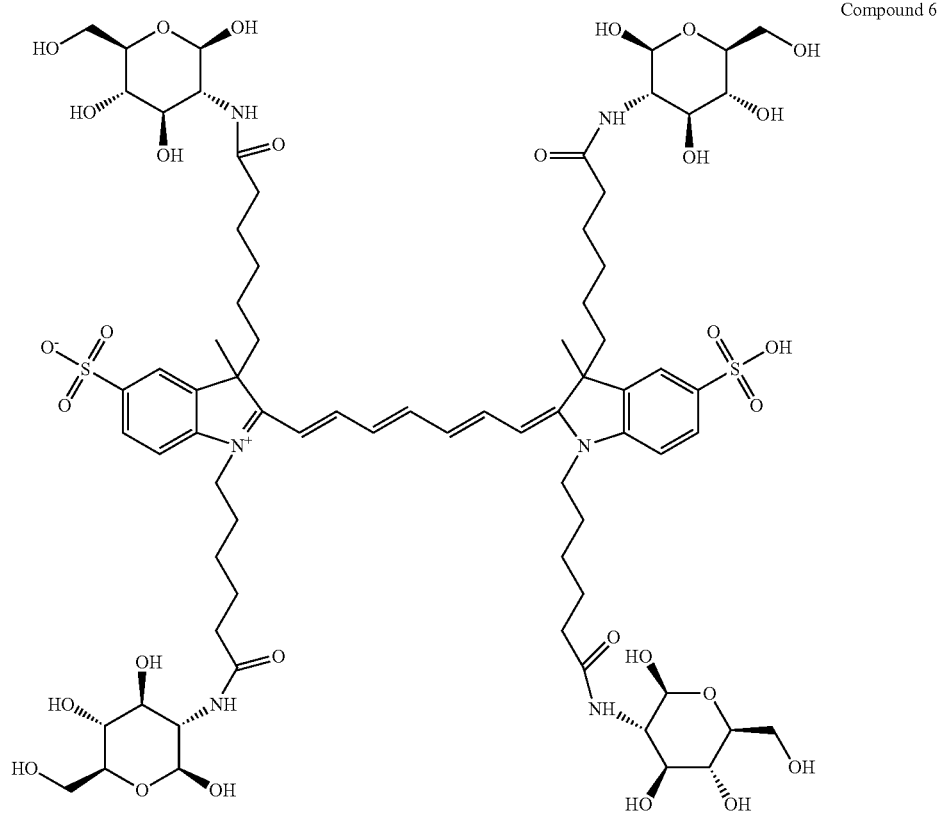 [SMILES: CC1(CCCCCC(=O)N[C@@H]2[C@@H](O)[C@H](O)[C@@H](CO)O[C@H]2O)C(/C=C/C=C/C=C/C=C2/N(CCCCCC(=O)N[C@H]3[C@H](O)[C@@H](O)[C@H](CO)O[C@@H]3O)c3ccc(S(=O)(=O)O)cc3C2(C)CCCCCC(=O)N[C@H]2[C@H](O)[C@@H](O)[C@H](CO)O[C@@H]2O)=[N+](CCCCCC(=O)N[C@H]2[C@H](O)[C@@H](O)[C@H](CO)O[C@@H]2O)c2ccc(S(=O)(=O)[O-])cc21]

Compound 6

Example 2

Imaging of Multivalent Fluorescent Probes

A. Glucose-Transport

A multivalent 2-deoxy-D-glucose Iflour750 (2-DG-IF750) probe for monitoring glucose transport and cell uptake was prepared such that each 2-DG-IF750 molecule contained flour 2-DG (Merck Index, 11th Edition, 2886) and one IFluor750 dye, essentially as described in Example 1. 2 Deoxy-D-glucose (2-DG) is uptaken by the glucose transporter of the cell. However, because 2-DG is unable to undergo glycolysis due to replacement of the 2-hydroxyl group by hydrogen, it accumulates in the cells upon uptake. The presence of near infrared fluorescence moiety in the 2-DG-IF750 probe allows fluorescence detection of cells/tissues that have high rate of glucose uptake, including tumor cells.

Accordingly, the presence of 2-DG-IF750 probe was evaluated in a subcutaneous LL2 tumor model. Briefly, C57 BL/6 mice were injected subcutaneously with $1 \times 10^6$ LL2-luc tumor cells (Caliper). At two weeks post injection, tumors were approximately 200 mm3. Mice were intravenously injected with 10 nmol of 2-DG-IF750, control IF750 dye or bioluminescent 2-DG. Mice were imaged at 3, 7, 24 and 72 hours using the IVIS Spectrum (Ex745 nm/Em820 nm) (Caliper).

Figure 2:
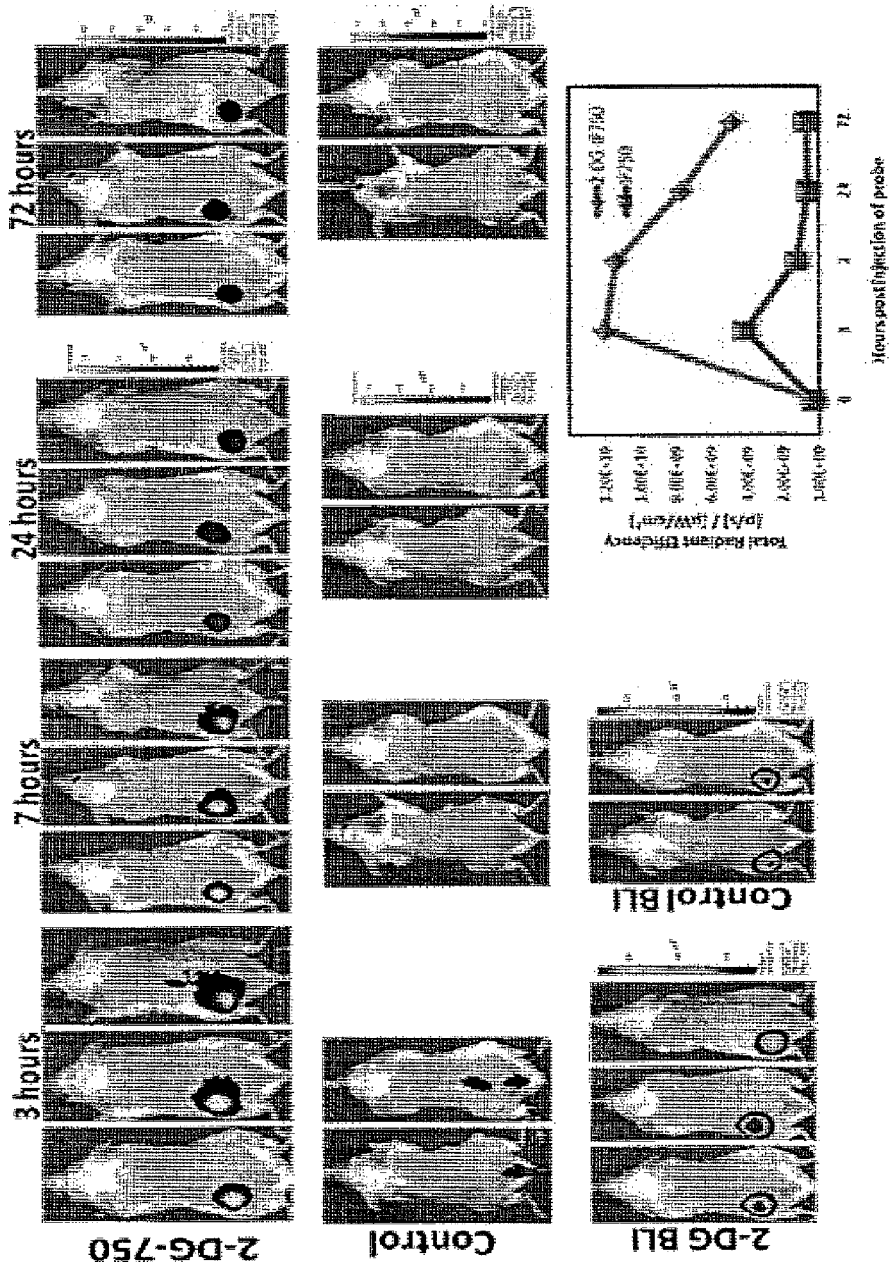
FIG. 2 depicts images of mice having subcutaneous tumors injected with the indicated probes and imaged at the indicated time points. "2-DG-750" refers to the multivalent fluorescent probe. Each probe included one molecule of IF750 fluorescent dye linked to at least 4 molecules of 2-deoxy-D-glucose. "Control" refers to mice injected with the fluorescent dye IF750 alone and "2-DG BLI" refers to animals injected with a bioluminescent probe. The graph shows total radiation efficiency of animals imaged after injection of the multivalent 2-DG-750 probe (diamonds) as compared to the control animals (squares).

As shown in FIG. 2, strong fluorescence signals were seen from the tumors when mice injecting with the multivalent 2-DG-IF750 probe, with a peak signal at 3 hours. The signals persisted for at least 72 hours, indicating that the probe had been up-taken by the tumors. Control mice that were injected with IF750 dye did not show any tumor labeling. Bioluminescence imaging showed similar luciferase activity in all the mice, which also correlated with tumor volume.

B. Multivalent COX-Binding Fluorescent Probes

A multivalent cyclooxygenase (COX) binding fluorescence probe, Indomethacin-IF750, was constructed by linking 4 indomethacin molecules to one IF750 molecule. Indomethacin is a non-selective COX inhibitor that binds to both cyclooxygenase isoforms COX1 and COX2 and inhibits prostaglandins synthesis. Each Indomethacin-IF750 molecule contains flour indomethacin and one IFlour750 dye molecules. The COX-1 enzyme is constitutively expressed in most mammalian cells. COX-2, on the other hand, is an inducible enzyme which is undetectable in most normal tissues but is abundant in activated macrophages and other cells at sites of inflammation. In colon cancer cell line HCT116 and HT29, COX2 is differentially expressed. HT29 cells showed high abundance of COX2 and HCT116 cells had low expression level.

The in vivo targeting property of the multivalent Indomethacin-IF750 was evaluated in mice with subcutaneous HCT116 and HT29 tumors. Briefly, Nu/Nu mice were injected subcutaneously with $2 \times 10^6$ tumor cells each of HCT11 (into left flank) and HT29 (right flank). The tumor cells were allowed to grow for 16 days, after which most had reaches approximately 100 nm3 in size. At day 16 following tumor cell introduction, mice were injected intraperitoneally with either the multivalent Indomethacin-IF750 probe (3 mg/kg) or the control IF750 dye. Mice were imaged at 3, 6, 24 and 96 hours after fluorescent probe or dye injection using the IVIS Spectrum (Ex745 nm/Em820 nm) (Caliper).

As shown in FIG. 3, we observed a specific labeling of the COX2 negative HCT116 tumors at 24 hours. In contrast, the COX2 positive HT29 tumors remained unlabelled. Binding of the Indomethacin-IF750 probe to the HCT116 tumor was long-lasting. The fold of difference between HCT116 and HT29 was 3.2 at 24 hours after injection and increased to 6.2 fold at 96 hours, due to a more rapid clearance of the background signal from HT29 tumors after probe injection. Thus, the indomethacin moiety, when placed in a multivalent setting, exhibits reduced affinity to COX2.

C. Multivalent RGD Fluorescent Probes

A multivalent RGD (arginine-glycine-aspartic acid) probe was constructed by linking 4 RGD molecules to a one IF750 fluorescent molecule ("RGD4" probe).

The in vivo targeting property of the multivalent Indomethacin-IF750 was evaluated in mice with subcutaneous prostate tumors. Briefly, PC3M-luc2 or U87-MG-luc2 human prostate cells (Caliper Life Sciences Bioware) were implanted subcutaneously into the flank regions of the mice. Following tumor growth, two nmol of one of the following probes was injected into a mouse by tail vein injection: RGD4, RGD-HPM2, RGD3500 or RGD2900. Mice were imaged at 3, 6, 24 and 48 hours after probe injection using the IVIS Spectrum (Ex745 nm/Em800 nm) (Caliper Life Sciences).

As shown in FIGS. 4 and 5, the RGD4 probe (FIGS. 4A and 5A) specifically labeled the tumor cells at higher levels than the RGD-HPM2 probe.

D. DPA-Zn Probes

Nu/Nu mice were injected with $1\times10^5$ cfu of bacteria subcutaneously at the scruff area in duplicate with either single-valent dicolylamine (DPA)-ifluor750 fluorescent probes (DPA) or tetra-valent (DPA)-ifluor750 fluorescent probes (DPA-tetra). See, FIG. 6 and Compound 6 above. As controls, mice were injected with Lipopolysaccharide (LPS, 1 mg/kg) in the left flank and PBS in the right flank. Mice were then intravenously injected with either DPA probe (10 nmol/mouse, n=3) or with DPA-tetra (10 nmol/mouse, n=3).

Figure 7B:
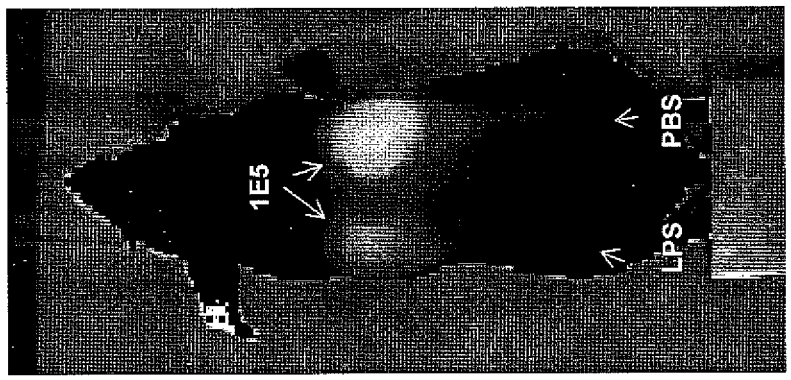
FIGS. 7A and 7B, depict imaging of bacterial infection in mice.
Figure 7A:
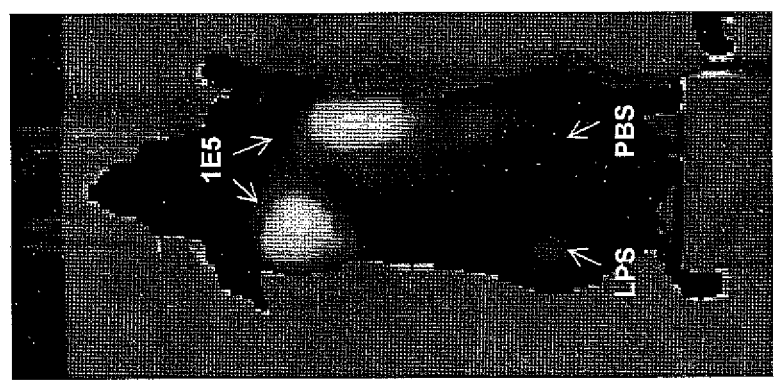
Figure 8A:
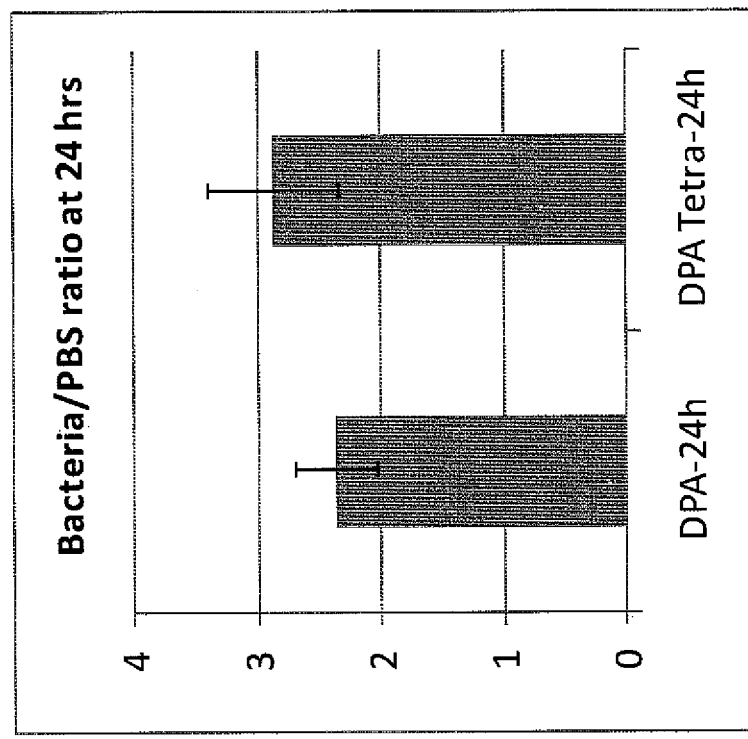
FIGS. 8A and 8B, are graphs depicting quantification of the signal from the mice imaged as described in Example 2 and shown in FIG. 7.
Figure 8B:
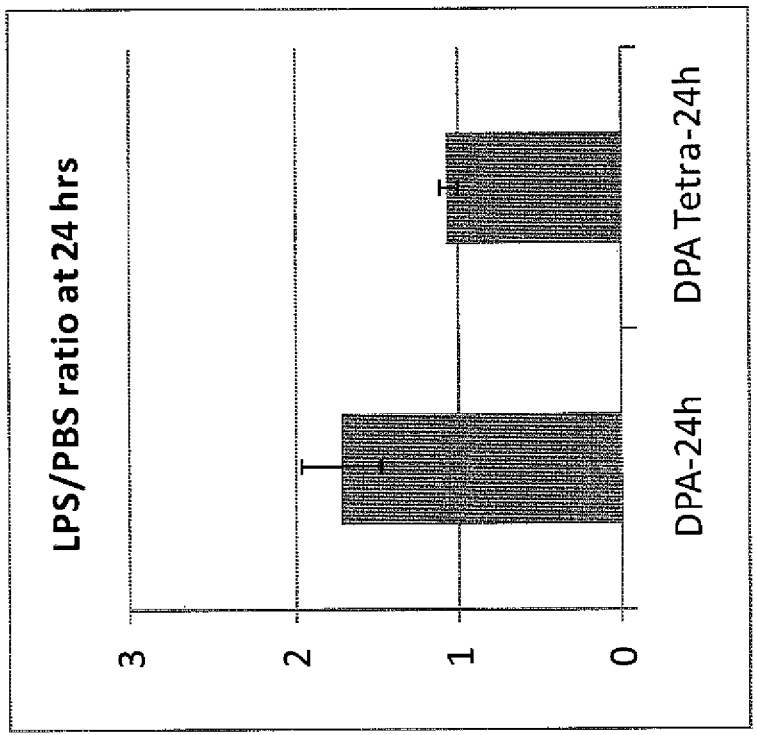

At 24 hours after probe injection, mice were imaged as described above for fluorescence signals. FIG. 7A shows imaging of mice injected with DPA probe and FIG. 7B shows mice injected with DPA-tetra probe. Furthermore, as shown in FIGS. 8A and 8B, the signals from the site of *Pseudomonas aeruginosa* injections were quantified, which showed that the DPA tetra probe (which includes 4 bis(zinc(II)-dicolylamine targeting moieties per probe, see, e.g., FIG. 6B) exhibited greater specificity for bacterial targeting based on the ratio of the bacterial signal over the background PBS signal as compared to the DPA-probe (which includes a bis(zinc(II)-dicolylamine. The DPA probe detected fluorescence signals from LPS injected sites, indicating this probe may bind to infiltrating inflammatory cells as instigated by the LPS challenge. Furthermore, the lack of (or much reduced) signal at the LPS sites in "DPA-tetra" injected mice indicates that the multivalent probes as described herein allow for specific detection of bacterial infection (as compared to the DPA probes, containing fewer than 3 moieties).

Thus, compositions and methods as described herein can be used to for imaging in vitro and in living animals. Although preferred embodiments have been described in some detail, it is understood that obvious variations can be made without departing from the spirit and the scope of the disclosure.

What is claimed is:

1. A method of detecting light from a sample or subject, the method comprising (a) administering to the sample or subject one or more multivalent fluorescent probes having the structure:

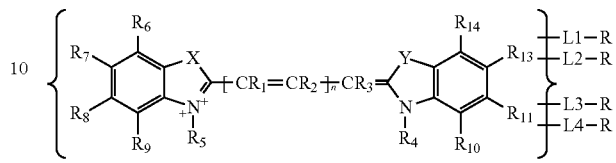

wherein X and Y are O, S, Se or $CR_{15}R_{16}$; n is 0 to 3; $R_1$ to $R_{11}$, and $R_{13-16}$ are independently selected from the group consisting of hydrogen, alkyl having 1 to 20 carbons, alkoxy having 1 to 20 carbons, trifluoromethyl, halogen, methylthio, sulfonyl, carbonyl, hydroxy, amino and thiol;

wherein R represents a targeting moiety and the four targeting moieties are linked to X, Y, N and N+ via the L1, L2, L3 and L4, wherein L1, L2, L3, and L4 are linkers and comprise 10 to 50 linear atoms selected from carbon, nitrogen, oxygen, phosphorus and sulfur that are further substituted by hydrogen, alkyl having from 1 to 20 carbons, alkoxy having from 1 to 20 carbons, trifluoromethyl, halogen, methylthio, sulfonyl, carbonyl, hydroxy, amino, thiol, amino acid residues RGD, zinc (Zn) or a ligand that binds to a cell surface receptor;

wherein the probe emits light having a wavelength of 550 to 1200 nm and wherein the targeting moiety is a molecule that specifically targets the multivalent fluorescent probe to a specific cell present in the sample or the subject;

(b) exposing the sample or subject to light of a wavelength of light that excites the fluorochrome of the fluorescent probe; and (c) detecting light emitted by the fluorescent probe.

2. The method of claim 1, wherein at least two of the targeting moieties are the same targeting moieties.

3. The method of claim 1, wherein at least two of the targeting moieties are different.

4. The method of claim 1, wherein at least one targeting moiety is selected from the group consisting of a small molecule, a sugar, a polypeptide, a cytokine, a neurotransmitter and combinations thereof.

5. The method of claim 1, further comprising, after step (a), the step of allowing the fluorescent probe time to localize in the sample or subject.

6. The method of claim 1, further comprising repeating steps (b) and (c) at predetermined intervals.

7. The method of claim 1, further comprising the step of constructing an image from the light emitted.

8. The method of claim 1, where in the sample is selected from the group consisting of a cell culture system, a cell lysate, an isolated tissue sample, a urine sample, a blood sample or combinations thereof.

9. The method of claim 1, wherein the subject is an animal.

10. The method of claim 9, wherein steps (b) and (c) are performed using an endoscope, a camera (e.g., CCD camera), a catheter, a tomographic system, a hand-held optical imaging systems, surgical goggles, or an intraoperative microscope.

11. The method of claim 10, further comprising imaging the animal using one or more additional imaging methods.

12. The method of claim 11, wherein the additional imaging methods are selected from the group consisting of PET, MRI, CT, and X-ray.

* * * * *